(12) United States Patent
Langer et al.

(10) Patent No.: US 10,660,863 B2
(45) Date of Patent: May 26, 2020

(54) TRANSDERMAL THERAPEUTIC SYSTEM FOR ADMINISTERING AN ACTIVE SUBSTANCE

(75) Inventors: Britta Langer, Berlin (DE); Björn Schurad, Munich (DE); Heike Prinz, Unterhaching (DE)

(73) Assignee: Luye Pharma AG, Miesbach (DE)

( * ) Notice: Subject to any disclaimer, the term of this patent is extended or adjusted under 35 U.S.C. 154(b) by 9 days.

(21) Appl. No.: 13/994,242

(22) PCT Filed: Dec. 14, 2011

(86) PCT No.: PCT/EP2011/072812
§ 371 (c)(1),
(2), (4) Date: Aug. 13, 2013

(87) PCT Pub. No.: WO2012/080365
PCT Pub. Date: Jun. 21, 2012

(65) Prior Publication Data
US 2014/0323996 A1 Oct. 30, 2014

(30) Foreign Application Priority Data
Dec. 14, 2010 (EP) .................................... 10194968

(51) Int. Cl.
*A61K 31/27* (2006.01)
*A61K 9/00* (2006.01)
*A61K 9/70* (2006.01)

(52) U.S. Cl.
CPC ............ *A61K 9/7084* (2013.01); *A61K 31/27* (2013.01)

(58) Field of Classification Search
None
See application file for complete search history.

(56) References Cited

U.S. PATENT DOCUMENTS

| 6,335,031 B1 | 1/2002 | Asmussen et al. |
| 6,689,379 B1 | 2/2004 | Bracht |
| 7,858,114 B2 | 12/2010 | Ito |

(Continued)

FOREIGN PATENT DOCUMENTS

| DE | 19918106 A1 | 10/2010 |
| EP | 1047409 A1 | 11/2000 |

(Continued)

OTHER PUBLICATIONS

Definition of "Coherent", Merriam Webster Dictionary Online, Accessed Apr. 2019. (Year: 2019).*

(Continued)

*Primary Examiner* — Brian Gulledge
(74) *Attorney, Agent, or Firm* — Curatolo Sidoti Co., LPA; Salvatore A. Sidoti; Floyd Trillis, III

(57) ABSTRACT

The present invention relates to a transdermal therapeutic system for administering an active substance through the skin, said system being suitable for an application period of at least three days, comprising the layers arranged in the following order with respect to each other:
a) a cover layer,
b) an active substance layer comprising a polymer matrix containing the active substance,
c) an adhesive layer comprising a contact adhesive, which consists of a mixture of one or more polyisobutylenes and one or more polybutenes, and
d) a pull-off layer.

29 Claims, 9 Drawing Sheets

(56) References Cited

U.S. PATENT DOCUMENTS

Figure 1:
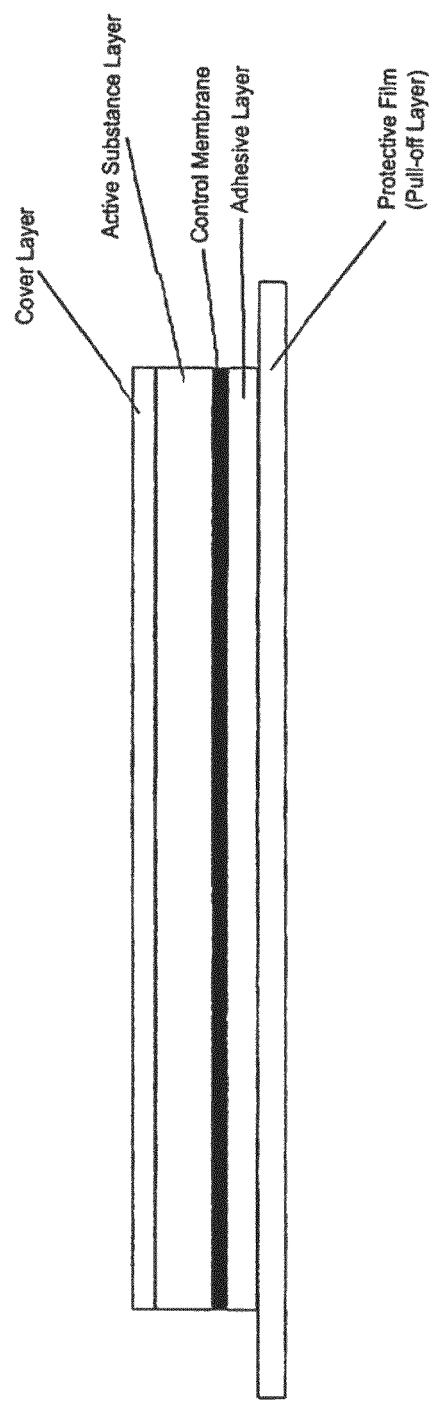

| | | | |
|---|---|---|---|
| 8,962,014 B2 * | 2/2015 | Prinz et al. | 424/449 |
| 2004/0086552 A1 | 5/2004 | Klokkers et al. | |
| 2004/0241219 A1 | 12/2004 | Hille et al. | |
| 2007/0128263 A1 * | 6/2007 | Gargiulo et al. | 424/449 |
| 2007/0259028 A1 * | 11/2007 | Ito | 424/449 |
| 2008/0044461 A1 | 2/2008 | Valia et al. | |
| 2008/0175890 A1 | 7/2008 | Yum et al. | |
| 2008/0260811 A1 | 10/2008 | Yum et al. | |
| 2009/0171258 A1 * | 7/2009 | Stroebeck et al. | 602/54 |
| 2009/0291127 A1 * | 11/2009 | Wen et al. | 424/449 |
| 2010/0292660 A1 | 11/2010 | Kydonieus | |
| 2011/0059141 A1 | 3/2011 | Ito | |
| 2013/0261571 A1 * | 10/2013 | Prinz et al. | 604/307 |

FOREIGN PATENT DOCUMENTS

| | | | | |
|---|---|---|---|---|
| EP | 2016939 A1 | 1/2009 | | |
| GB | 2203040 A | 10/1988 | | |
| WO | WO 02/03969 A2 | 1/2002 | | |
| WO | WO 03/017988 A1 | 3/2003 | | |
| WO | WO 2007/064407 A1 | 6/2007 | | |
| WO | WO 2008/021113 A2 | 2/2008 | | |
| WO | WO 2009/009651 A1 | 1/2009 | | |
| WO | WO 2009/026135 A2 | 2/2009 | | |
| WO | WO2011/076621 | * | 6/2011 | A61K 9/70 |

OTHER PUBLICATIONS

Definition of "Cohering", Merriam Webster Dictionary Online, Accessed Apr. 2019. (Year: 2019).*

PCT/EP2011/072812—International Search Report, dated May 16, 2012.

PCT/EP2011/072812—International Written Opinion, dated May 16, 2012.

PCT/EP2011/072812—International Preliminary Report on Patentability, dated Jun. 18, 2013.

* cited by examiner

TRANSDERMAL THERAPEUTIC SYSTEM FOR ADMINISTERING AN ACTIVE SUBSTANCE

CROSS REFERENCE TO RELATED APPLICATIONS

This application is a national stage application of International Application No. PCT/EP2011/072812, filed 14 Dec. 2011, which claims priority from European Patent Application No. EP 10194968.3, filed 14 Dec. 2010, from which applications priority is claimed, and which are incorporated herein by reference.

The object of the present application is a system for the transdermal administration of an active substance, preferably rivastigmine, its physiologically compatible salt, hydrate, solvate, or derivative that is suitable for a therapeutic application period of several days.

Rivastigmine is the phenylcarbamate (S)-N-ethyl-3-[(1-dimethylamino)ethyl]-N-methylphenyl-carbamate of the formula I.

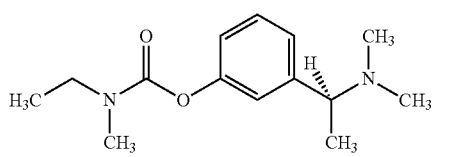

(I)

It is a cholinesterase inhibitor acting in the central nervous system and thus, is an active substance for the treatment of the Alzheimer's disease and Parkinson's dementia.

Rivastigmine may be present as a free base, but also as an acid addition salt, hydrate, solvate, or as another derivative. These derivatives are encompassed in der present invention with the designation "rivastigmine", unless otherwise described.

A preferred form to administer rivastigmine is the percutaneous administration by means of a transdermal therapeutic system, that is a transdermal patch. Typically, a transdermal patch is a small self-adherent bandage containing the active substance to be delivered. These bandages can have various forms and sizes. The simplest type is an adhesive monolith comprising an active substance stock on a carrier (cover layer). This active substance stock is typically formed in the form of an active substance layer of the active substance in a pharmaceutically acceptable pressure-sensitive adhesive or contact adhesive and is in contact with the skin area, whereby the active substance is delivered into the body of the patient by transdermal diffusion.

More complex patches are multiple laminates or patches with an active substance stock, wherein a further adhesive layer can be arranged between the active substance layer and the skin.

One form of administration via transdermal patches of rivastigmine has been already described in the basic patent on rivastigmine, GB 2203040. The transdermal patch disclosed therein consists of a cover layer and a layer forming the active substance layer. In addition to the active substance rivastigmine a hydrophilic polymer, a non-swelling acrylate polymer, and a plasticizer are contained in the active substance layer.

After publication of the GB 2203040 further transdermal therapeutic systems (TTS) i.a. containing rivastigmine as active substance have been developed and described. In WO 02/03969 a TTS is described, wherein the active substance-containing matrix layer additionally contains highly disperse silica for increasing the skin permeation.

In the patent applications WO 2008/021113 and EP 2 016 939 there are disclosed patches with a more complex structure that intended to ensure an administration of different active substances over a period of up to seven days. These patches, between the layer containing the active substance and an adhesive layer, additionally contain a membrane controlling the delivery of the active substance. However, in the active substance layer of the patch free hydroxyl groups are present, because a polyhydric alcohol is contained in the active substance layer.

In DE 199 18 106 the active substance layer contains a self-adhesive polymer having acrylic acid or methacrylic acid units with a defined content of carboxyl groups to increase the water-absorbing capacity as well as tolerance of acidic polyacrylic contact adhesives to moisture.

WO 20071064407 A1 discloses a TTS with a silicone-based adhesive layer to achieve an improvement in terms of the adhesive properties, tolerance, and safety in the rivastigmine therapy. According to WO 2007/064407 A1 it is particularly preferred that the reservoir layer contains an antioxidant (page 7, $4^{th}$ paragraph). Accordingly, all formulations in the examples contain the antioxidant vitamin E. The Durotak® 387-2353 used there is a polyacrylate having carboxyl groups. According to WO 2007/064407 A1, the reservoir layer is also supposed to contain as penetration enhancer various substances such as, e.g. glycerin, fatty acids, etc. (page 7, $5^{th}$ paragraph). These substances often contain free hydroxyl or carboxyl groups that are thus present in the polymer matrix of the reservoir layer. WO 20071064407 A1 does not specially deal with the stability of rivastigmine. In particular. WO 2007/064407 A1 does not teach to select certain polymers for the polymer matrix of the reservoir layer to prevent the degradation of rivastigmine.

US 2008/0044461 A1 discloses TTS formulations with donepezil (see examples). Rivastigmine is also mentioned (claim 7). US 2008/0044461 A1 does not disclose any active substance layer with a polymer matrix. Rather, the release is controlled via a membrane (so-called membrane patches), not via a polymer skeleton into which the active substance is embedded (so-called matrix patches). Moreover, it is an essential feature of US 2008/0044461 A1 that the reservoir layer contains a gel-forming agent and a permeation enhancer (see claim 1). Alcohols are used as the permeation enhancers (see. [0053]). Cellulose polymers are used as the gel-forming agents (see. [0055]). Thus, both the permeation enhancers and the gel-forming agents are compounds with free hydroxyl groups that are present in the TTS in the reservoir layer.

US 2007/0259028 A1 discloses TTS formulations with donepezil (see, examples). Rivastigmine is also mentioned (claim 3). It is an essential feature of US 2007/0259028 A1 that the reservoir layer contains a polyhydric alcohol, e.g. glycerin. That is, according to US 2007/0259028 A1 free hydroxyl groups are inevitably present in the polymer matrix of the reservoir layer.

US 2004/0086552 A1 discloses TTS formulations with an active substance that can be selected from a very long list (see [0070] to [0095]). Both matrix patches and "membrane patches" are disclosed (see [0057] and [0058], respectively). For the matrix patches. US 2004/0086552 A1 does not teach to select certain polymers for the matrix to stabilize the active substance.

U.S. Pat. No. 6,689,379 B1 discloses TTS formulations with a particular adhesive layer. Also, rivastigmine is mentioned as a possible active substance. Preferably, the active substance layer is supposed to contain a compound with hydroxyl groups, see claim 10. U.S. Pat. No. 6,689,379 B1 does not teach to select certain polymers for the polymer matrix of the reservoir layer to prevent the degradation of rivastigmine.

However, the patent EP 1 047 409 reports a general problem with the administration of rivastigmine by a TTS. It has been found that especially in the presence of oxygen the active substance is susceptible to decomposition. In der transdermal composition disclosed in GB 2203040 the rivastigmine decomposes according to the disclosure in EP 1 047 409 also despite the formation of a closed polymer matrix around the active substance and an airtight package of the composition. In EP 1 047 409 the problem of the low stability of rivastigmine is solved in that an antioxidant is added to the pharmaceutical composition.

Up to now, commercially acquirable TTS with rivastigmine permit only a continuous administration over 24 hours. One object of the invention is to control the release over the extended time interval. With the transdermal administration of rivastigmine over a prolonged period it has to be ensured that (1) a sufficient chemical stability of the active substance rivastigmine is guaranteed, (2) a sufficient physical stability (in particular in terms of cold flow) of the system is guaranteed, and (3) the system has a sufficient adhesiveness over the application period.

A further object of the present invention is to find therapeutic compositions containing rivastigmine for the transdermal administration that are suitable for a therapeutic application period of several days.

SUMMARY OF THE INVENTION

It has been found that rivastigmine in transdermal patches is sufficiently stable if the polymer matrix of the active substance layer does not contain any free hydroxyl groups or carboxyl groups. The present invention is based, inter alia, on the selection of special polymers for the polymer matrix to thereby prevent or minimize, respectively, the degradation of rivastigmine.

Thus, the present invention provides a sufficiently stable TTS containing rivastigmine and a method for the production of the same.

Thus, a first aspect of the present invention is a TTS for administering rivastigmine for an application period of several days, which comprises the following components:
   a) a cover layer,
   b) an active substance layer on the cover layer which comprises an active substance-containing polymer matrix.
   c) a membrane on the active substance layer which controls the release of rivastigmine;
   d) an adhesive layer on the membrane which comprises a contact adhesive; and
   e) a pull-off layer on the adhesive layer,
wherein the polymer(s) of the active substance layer do(es) not contain any free hydroxyl groups or carboxyl groups.

Moreover, the invention provides the use of polymers or copolymers without any free hydroxyl groups or carboxyl groups in a TTS containing rivastigmine and a TTS for the treatment of the Alzheimer's disease and Parkinson's dementia.

Although in WO 2008/021113 the adhesive materials polyisobutylene, polyacrylate, and silicone-based adhesives are described as equally suitable it has presently been found that polyisobutylenes are better suited as contact adhesive in the adhesive layer and that the properties of this adhesive are further improved by the addition of polybutene as a tackifier. Thus, the present invention provides a TTS containing an active substance and having improved adhesive properties, and a method for the production of the same.

Thus, a second aspect of the present invention is a transdermal therapeutic system for administering an active substance through the skin comprising the layers arranged in the following order with respect to each other
   a) a cover layer,
   b) an active substance layer comprising a polymer matrix containing the active substance,
   c) an adhesive layer comprising (1) a contact adhesive which consists of a polyisobutylene or a mixture of several polyisobutylenes, and (2) an adhesive enhancer which consists of polybutene or a mixture of several polybutenes; and
   d) a pull-off layer.

A third aspect of the present invention is a TTS for administering rivastigmine through the skin comprising a cover layer, an active substance layer containing the rivastigmine, the adhesive layer improved according to the second aspect, and a pull-off layer for the administration of rivastigmine over a period of at least two (e.g. two or three) days wherein a membrane controlling the release of rivastigmine is present between the active substance layer and the adhesive layer. Thus, a third aspect of the present invention is a tranadermal therapeutic system for administering an active substance through the skin comprising the layers arranged in the following order with respect to each other.
   a) a cover layer,
   b) an active substance layer comprising an active substance-containing polymer matrix,
   c) a membrane controlling the release of the rivastigmine:
   d) an adhesive layer comprising (1) a contact adhesive which consists of a polyisobutylene or a mixture of several polyisobutylenes, and (2) an adhesive enhancer which consists of polybutene or a mixture of several polybutenes: and
   e) a pull-off layer.

A fourth aspect of the present invention is a TTS for administering rivastigmine through the skin comprising a cover layer, an active substance layer containing rivastigmine, the adhesive layer improved according to the second aspect, and a pull-off layer, wherein the active substance layer has no free hydroxyl groups or carboxyl groups. Thus, the fourth aspect of the present invention is a transdermal therapeutic system for administering an active substance through the skin comprising the layers arranged in the following order with respect to each other:
   a) a cover layer,
   b) an active substance layer comprising a polymer matrix containing the active substance,
   c) an adhesive layer comprising (1) a contact adhesive which consists of a polyisobutylene or a mixture of several polyisobutylenes, and (2) an adhesive enhancer which consists of polybutene or a mixture of several polybutenes, and
   d) a pull-off layer.
wherein the polymer(s) of the active substance layer does not contain any free hydroxyl groups or carboxyl groups.

A fifth aspect of the present invention is the provision of a TTS for administering rivastigmine through the skin comprising a cover layer, an active substance layer containing the rivastigmine, the adhesive layer improved according to the invention, and a puff-off layer, wherein at least the active substance layer, but preferably the entire TTS, has no antioxidants. Thus, the fifth aspect of the present invention is a transdermal therapeutic system for administering an active substance through the skin comprising the layers arranged in the following order with respect to each other:
a) a cover layer,
b) an active substance layer comprising a polymer matrix containing the active substance,
c) an adhesive layer comprising (1) a contact adhesive which consists of a polyisobutylane or a mixture of several polyisobutylenes, and (2) an adhesive enhancer which consists of polybutene or a mixture of several polybutenes, and
d) a pull-off layer,
wherein at least the active substance layer, but preferably the entire TTS, has no antioxidants.

The above-mentioned various aspects of the invention can be arbitrarily combined with each other. The active substance within the meaning of the present invention is rivastigmine or a physiologically compatible salt, hydrate, solvate, or derivative thereof.

DETAILED DESCRIPTION OF THE INVENTION

Definitions

An "antioxidant" within the meaning of the present invention is a pharmaceutically acceptable compound or composition that decelerates, inhibits, disrupts, and/or retards the oxidation processes. In particular, antioxidants include the following substances: tocopherolis and their esters, the Sesamol of sesame oil, the coniferyl benzoate of benzoin, nordihydroguaiac resin and -guaiaretic acid (NDGA), gallates (methyl, ethyl, propyl, amyl, butyl, lauryl a.o. gallates), butylated hydroxyanisole (BHT, also called butyl-p-cresol); ascorbic acid and salts and esters thereof (e.g. ascorbyt palmitate), erythorbic acid (iso-ascorbic acid) and salts and esters thereof, monothioglycerol, sodium formaldehyde sulfoxylate, sodium metabisulfite, sodium bisulfite, sodium sulfite, potassium metabisulfite, butylated hydroxyanisole, butylated hydroxytoluene, propionic acid.

The term "tocopherol" also includes tocopherol esters. A known tocopherol is α-tocopherol. The term "α-tocopherol" includes esters of α-tocopherol (e.g. α-tocopherol acetate).

A "polymer matrix" is a solid or semi-solid composition having a three dimensional structure which comprises a polymer or a mixture of polymers. The polymer matrix is also referred to as polymer skeleton since the three dimensional skeleton structure is as a rule provided by the polymer or mixture of polymers. Other substances, e.g. an active substance, may be embedded in the polymer matrix. Preferably, the active substance is evenly distributed in the polymer matrix.

In the following, the features of the TTS according to the invention are described in more detail and, unless it is explicitly stated otherwise, the respective explanations on the individual features refer to all of the preceding aspects of the present invention.

Moreover, the preceding aspects of the present invention can be arbitrarily combined to further preferred embodiments. So, for example in a preferred TTS the active substance layer is free of tocopherols, and the polymer(s) of the polymer matrix of said active substance layer contain(s) neither hydroxyl groups nor carboxyl groups. Additionally, in this embodiment a membrane controlling the release of rivastigmine is preferably present between the active substance layer and the adhesive layer, and the TTS is suited for an application period of at least two, at least three or at least four days, e.g. for two to seven, for three to six, or for four to five days.

In the TTS according to the invention the active substance rivastigmine is sufficiently stable. "Sufficiently stable" means that the impurities of the active substance after one month of storage at 40° C. and 75% relative air humidity in total are not more than 1% by weight, preferably not more than 0.5% by weight, based on the desired content of active substance in the formulation. Impurities of the active substance in the formulation are degradation products of the active substance rivastigmine and impurities introduced with the active substance into the formulation (e.g. traces of intermediate products from the production of the active substance).

The stability and amount, respectively, of impurities can be determined as described in example 4. Preferably, the total content of the decomposition products/impurities after three months of storage at 40° C. and 75% relative air humidity is less than 1% by weight, preferably less than 0.6% by weight. It is also preferred that the total content of the decomposition products/impurities after six months of storage at 40° C. and 75% relative air humidity is less than 1% by weight. It is also preferred that the total content of impurities after one month of storage at 25° C. and 60% relative air humidity is less than 0.25% by weight. It is further preferred that the total content of impurities after three and after six months of storage at 25° C. and 60% relative air humidity is less than 0.5% by weight. The information on "% by weight" of impurities always refer to the desired content of active substance in the formulation, unless stated otherwise.

The application period of a TTS according to the invention is preferably at least two or at least three days. In a special embodiment the TTS according to the invention is suitable for an application period of 2 to 4, 2 to 5, 2 to 6, 2 to 7, or 3 to 8 days.

Preferably, the active substance layer, more preferably the entire TTS, has no tocopherol. In a further embodiment the active substance layer, preferably the entire TTS, has no tocopherol and no butylated hydroxyanisole (BHT, also called butyl-p-cresol) In a further embodiment the active substance layer, preferably the entire TTS, has no tocopherol, no butylated hydroxyanisole, and no butylated hydroxytoluene. In a particular embodiment the active substance layer, preferably the entire TTS, has none of the following antioxidants: tocopherots and their esters, the Sesamol of sesame oil, the coniferyl benzoate of benzoin, nordihydroguaiac resin and -guaiaretic acid (NDGA), gallates (methyl, ethyl, propyl, amyl, butyl, lauryl a.o. gallates), butylated hydroxyanisole (BHT, also called butyl-p-cresol); ascorbic acid and salts thereof, ascorbyl palmitate, erythorbic acid (iso-ascorbic acid) and salts thereof, monothioglycerol, sodium formaldehyde sulfoxylate, sodium metabisulfite, sodium bisulfite, sodium sulfite, potassium metabisulfite, butylated hydroxyanisole, butylated hydroxytoluene, propionic acid. In a special embodiment the active substance layer, more preferably the entire TTS, has no antioxidants at all.

However, it is quite possible that in the TTS of the present invention antioxidants can be present as long as these do not negatively affect the TTS's mode of action. Here, it has to be noted that for stabilizing rivastigmine according to one aspect of the present invention no antioxidants are necessary. However, antioxidants can also be employed for other purposes in the TTS according to the invention. Thus, it is possible, although not preferred, that the TTS according to the invention does contain antioxidants, e.g. tocopheros such as α-tocopherol and its esters, butylated hydroxytoluene and butylated hydroxyanisole.

The total amount of antioxidant in the TTS of the present invention is typically less than 1% by weight or less than 0.1% by weight, more preferably less than 0.05% by weight, most preferably less than 0.01% by weight, each based on the weight of the total formulation (without cover and pull-off layer).

Structure of the TTS

The structure of the TTS according to the invention comprises several layers. The cover layer is on the end of the TTS that is in use turned away from the skin. The active substance layer is at the side of the cover layer that faces the human skin in use. Moreover, the adhesive layer is at the side of the active substance layer that faces the human skin in use. Before the TTS is used, the pull-off layer is at the side of the adhesive layer that faces the human skin in use, which is removed right before the use of the TTS. Preferably, a membrane controlling the release of the active substance is present between the active substance layer and the adhesive layer.

The area of the TTS according to the invention is not particularly limited. Typically, the area is about 5-40 $cm^2$, but can thoroughly be greater or smaller.

In one embodiment, the area of the cover layer of the TTS according to the invention corresponds at least to the area of the active substance layer or the adhesive layer, respectively. However, it can also be greater than that of the active substance layer so that it not only completely covers the active substance layer but also extends beyond the edge of the active substance layer. However, in such an embodiment either the area of the adhesive layer should be equal to the area of the cover layer, or the side of the cover layer that faces the skin should have a further adhesive layer in order to ensure that the entire surface of the TTS that faces the skin in use adheres to the skin. In another embodiment the cover layer is somewhat smaller than the area of the active substance layer and/or adhesive layer.

Active Substance Layer

The active substance layer of the TTS according to the invention contains the active substance, preferably rivastigmine, embedded in a polymer matrix. According to the first aspect of the invention the polymer matrix comprises substantially no polymers or copolymers containing free hydroxyl groups or free carboxyl groups. Preferably, the polymer matrix contains substantially no free hydroxyl groups and no free carboxyl groups. Preferably, the polymer matrix contains substantially no free amino groups, no free hydroxyl groups, and no free carboxyl groups. Preferably, the polymer matrix is formed of polymers and/or copolymers containing substantially no free hydroxyl groups and no free carboxyl groups. Still more preferably, the polymer matrix is formed of polymers and/or copolymers containing no amino groups, no free hydroxyl groups, and no free carboxyl groups.

Suitable polymers or copolymers without free functional groups that form the polymer matrix are particular polyacrylates, acrylate-vinylacetate copolymers, polyisobutylene and styrene-butadiene copolymers which an be present individually or as blend.

As suitable polyacrylates containing substantially no free functional groups polymers (homopolymers, copolymers, and block-copolymers) on the basis of acrylic acid esters and/or methacrylic acid esters can be used. As monomers for the production of suitable polyacrylates here, in particular n-butyl acrylate, n-butyl methacrylate, ethyl acrylate, 2-ethylhexyl acrylate, ethyl methacrylate, methyl acrylate, methyl methacrylate, tert-butyl acrylate, sec-butyl acrylate, tert-butyl methacrylate, cyclohexyl methacrylate, 2-ethylhexyl methacrylate, isobornyl methacrylate, isobutyl methacrylate, isopropyl acrylate, isopropyl methacrylate and mixtures of these monomers are possible. These monomers are esters of the acrylic or methacrylic acid, respectively, that carry linear, branched or cyclic aliphatic $C_1$-$C_{12}$ substituents without other free functional groups. Also vinyl acetate can be used as a comonomer together with at least one of these monomers for the production of the polyacrylate.

Preferably, the polymer matrix consists of one or more polyacrylates containing substantially no free functional groups. More preferably, the polymer matrix consists of polyacrylates prepared by the polymerization of acrylic acid esters and/or methacrylic acid esters. In a particular embodiment, the polymer matrix consists of polyacrylates prepared by the polymerization of acrylic acid esters and/or methacrylic acid esters, with the acrylic acid esters and/or methacrylic acid esters being selected from the group consisting of n-butyl acrylate, n-butyl methacrylate, ethyl acrylate. 2-ethylhexyl acrylate, ethyl methacrylate, methyl acrylate, methyl methacrylate, tert-butyl acrylate, sec-butyl acrylate, tert-butyl methacrylate, cyclohexyl methacrylate, 2-ethylhexyl methacrylate, isobornyl methacrylate, isobutyl methacrylate, isopropyl acrylate, isopropyl methacrylate, and mixtures thereof. In another embodiment the polymer matrix substantially consists of polyacrylates prepared by the copolymerization of acrylic acid esters and/or methacrylic acid esters with vinyl acetate, wherein the acrylic acid esters and/or methacrylic acid esters are selected from the group consisting of n-butyl acrylate, n-butyl methacrylate, ethyl acrylate. 2-ethyihexyl acrylate, ethyl methacrylate, methyl acrylate, methyl methacrylate, tert-butyl acrylate, sec-butyl acrylate, tert-butyl methacrylate, cyclohexyl methacrylate, 2-ethyhexyl methacrylat, isobornyl methacrylate, isobutyl methacrylate, isopropyl acrylate, isopropyl methacrylate, and mixtures thereof.

Particularly preferred are copolymers prepared from the starting monomers 2-ethylhexyl acrylate and vinyl acetate, e.g. an acrylate-vinyl acetate copolymer which is prepared to 50% each of the starting monomers 2-ethylhexyl acrylate and vinyl acetate (Duro-Tak® 87-4098). Also preferred is the acrylate polymer Duro-Tak® 87-9088 (also an acrylate polymer without free functional groups) available from Henkel. In a special embodiment the acrylate polymer Duro-Tak® 87-900A or Duro-Tak® 87-9301 is used for the polymer matrix.

The total proportion of monomers containing free hydroxyl groups or free carboxyl groups (e.g. acrylic acid, methacrylic acid, and esters of the acrylic acid or methacrylic acid, respectively, that carry functional groups, in particular the hydroxyl groups-containing esters) is below 1% by weight, preferably below 0.5% by weight, more preferably below 0.2% by weight; based on the mixture of monomers the polymer matrix is prepared of. In a particular embodiment the total proportion of said monomers is below 0.1% by weight. In a particular embodiment no free hydroxyl groups and no free carboxyl groups are contained in the mixture of monomers.

Certainly, a TTS containing polyacrylates substantially free of hydroxyl groups and carboxyl groups as the active substance-containing polymer matrix has been already described in WO 03/017988 A1, but not in connection with the active substance rivastigmine. The object described in WO 03/017988 was to solve the drawback of the low active substance utilization of a TTS. According to this disclosure said object has been solved by polymer matrices which ideally are free of hydroxyl groups or carboxyl groups. In this printed matter, the active substance rivastigmine is not mentioned, let alone an effect enhancing the stability of rivastigmine.

According to one aspect of the invention the active substance layer contains substantially no polymers or copolymers containing free hydroxyl groups or free carboxyl groups. Preferably, the active substance layer contains substantially no free hydroxyl groups and no free carboxyl groups. More preferably, the active substance contains substantially no free amino groups, no free hydroxyl groups, and no free carboxyl groups. In a particular embodiment, also the adhesive layer contains substantially no polymers or copolymers containing free hydroxyl groups or free carboxyl groups. Preferably, the adhesive layer contains substantially no free hydroxyl groups and no free carboxyl groups. More preferably, the adhesive layer contains substantially no free amino groups, no free hydroxyl groups, and no free carboxyl groups.

Preferably, the active substance layer contains 30-50% by weight of rivastigmine and 50-70% by weight of the polymer matrix, based on the total weight of the active substance layer. In a particularly preferred embodiment of the TTS according to the invention the active substance layer contains about 40% by weight of rivastigmine and about 60% by weight of the polymer matrix. Preferably, the active substance layer in addition to the active substance and the polymer matrix contains no further constituents. However, it is possible that additionally further additives known in the prior art are contained in the active substance layer. Thus, for example plasticizers or gel-forming agents may additionally be present in the active substance layer.

The absolute amount of rivastigmine depends on different factors, in particular the size of the TTS to be used, the base weight, and the active substance concentration in the active substance layer. The base weights of the dried active substance layer matrix preferably are in the range of 20-100 g/m$^2$, more preferred in the range of 25-80 g/m$^2$, and still more preferred in the range of 30-70 g/m$^2$. The active substance layer can have a thickness (dry thickness) in the range of 20-400 µm or 30-200 µm or 40-100 µm. Also other thicknesses than those mentioned above are possible.

Intermediate Membrane

Preferably, the membrane that according to one aspect of the present invention lies between the active substance layer and the adhesive layer and controls the release of the active substances (also referred to as "control membrane") consists of a polyolefine such as for example polypropylene (e.g., Celgard® 2400) or particularly preferred of polyethylene (e.g., CoTran™ 9719 or CoTran™ 9720) or more preferably of polyethylene with a vinyl acetate proportion of 4.5 to 19% (e.g. CoTran™ 9707. CoTran™ 9702. CoTran™ 9728). Moreover, the membranes can have a porosity of up to 90% (e.g. Solupor® 10P05A, Celgard® 2400).

Porous membranes or coherent membranes may be used. The porosity of the porous membranes can be up to about 90%. Data of preferred porous membranes are:
Solupor® 10P05A (polyethylene, porosity: 83%, thickness: 60 µm)
Celgard® 2400 (polypropylene, porosity: 41%, thickness: 25 µm)
Data of preferred coherent membranes are:
CoTran™ 9719 (polyethylene, thickness: 43.2 µm)
CoTran™ 9720 (polyethylene, thickness: 76.2 µm)
C0oTran™ 9707 (polyethylene with 4.5% vinyl acetate, thickness: 50.8 µm)
CoTran™ 9702 (polyethylene with 9.0% vinyl acetate, thickness: 50.8 µm)
CoTran™ 9728 (polyethylene with 19.0% vinyl acetate, thickness: 50.8 µm)

Typically, the membrane has a thickness of 0.01 and 0.15 mm. The preferred thickness of the membrane is 0.025 to 0.080 mm.

According to the invention it is preferred to use a coherent membrane substantially consisting of polyethylene with a thickness of about 40 to 80 µm (e.g., CoTran™ 9720). According to the invention it is also preferred to use a coherent membrane substantially consisting of polyethylene with about 19.0% vinyl acetate (e.g. CoTran™ 9728). According to the invention it is most preferred to use a coherent membrane substantially consisting of polyethylene with a thickness of about 40 to 50 µm (e.g. CoTran™ 9719).

The membrane is the essential formulation constituent in order to ensure a controlled delivery of the active substance over several days. The drug delivery can be controlled by the vinyl acetate proportion in the membrane, inter alia.

Adhesive Layer

Preferably, the adhesive layer of the TTS according to the invention contains polyisobutylene as contact adhesive and optionally polybutene to improve the adhesiveness. Polyisobutylene is a self-adherent contact adhesive that does not cure and thus, maintains its adhesive properties over a long period. Preferably, polyisobutylenes with different average molecular weights as a mixture are used. Polyisobutylene is available in various average molecular weights. The term "average molecular weight" in connection with polyisobutylene in the present application refers to the so-called viscosity average $M_V$. The viscosity average $M_V$ is determined from the solution viscosity of a solution of the polyisobutylene in isooctane at 20° C. As the measuring device there is used an Ubbelohde viscometer. The viscosity average $M_V$ is calculated from the following equation:

$$M_v = \frac{0.65}{\sqrt{\frac{J_o \times 10^2}{3.06}}}$$

The estimation of the intrinsic viscosity $J_o$ required for the determination of the viscosity average $M_V$ is done according to the Schulz-Blaschke relationship from the specific viscosity $\eta_{SP}$ measured and the solution concentration.

$J_o = \eta_{sp}/c(1+0.31 \times \eta_{sp})$ cm$^3$/g (Schulze-Blaschke relationship)

The specific viscosity $\eta_{SP} = t/t_0 - 1$, wherein t and $t_0$ are the flow time of the solution or the solvent (each with Hagenbach-Couette correction), respectively, and c is the concentration of the solution in g/cm$^3$. Optionally, the regulation DIN 53728 may be additionally considered.

Suitable average molecular weights $M_V$ of polyisobutylene are for example in the range of about 40,000 g/mol to about 4,000,000 g/mol. A possible mixture is that of (1) polyisobutylene with an average molecular weight $M_V$ of about 40,000 g/mol (e.g., Oppanol® B10, available from BASF) and (2) polyisobutylene having an average molecular weight $M_V$ of more than about 1,000,000 g/mol (z. B. Oppanol® B100, available from BASF, with an average molecular weight $M_V$ of about 1,110,000 g/mol). It is within the knowledge of the skilled person to mix the various molecular weights in the suitable ratio such as to achieve the desired properties of the adhesive layer.

The polyisobutylene in the adhesive layer may have a molecular weight distribution having a first relative maximum between 30,000 g/mol and 100,000 g/mol, and a second relative maximum between 300,000 g/mol and 500,000 g/mol. More preferably, the first relative maximum is between 35,000 g/mol and 50,000 g/mol and independently, the second relative maximum is between 350,000 g/mol and 450,000 g/mol. Most preferably, the first relative maximum is about 40,000 g/mol, and independently, the second relative maximum is about 400,000 g/mol.

The polyisobutylene mixture of the contact adhesive can be obtained by mixing a first polyisobutylene polymer with an average molecular weight $M_V$ between 30,000 g/mol and 100,000 g/mol with a second polyisobutylene polymer with an average molecular weight $M_V$ between 300,000 g/mol and 500,000 g/mol. Preferably, the first polyisobutylene polymer has an average molecular weight $M_V$ between 35,000 g/mol and 50,000 g/mol, most preferably of about 40,000 g/mol. Preferably, the second polyisobutylene polymer has an average molecular weight $M_V$ between 350,000 g/mol and 450,000 g/mol, most preferably of about 400,000 g/mol.

The most preferred mixture is that of (1) polyisobutylene with an average molecular weight $M_V$ of about 40,000 g/mol (for example Oppanol® B10 SFN, available from BASF) and (2) polyisobutylene with an average molecular weight $M_V$ of about 400,000 g/mol (for example Oppanol® B50 SF, available from BASF).

The proportion of the two polyisobutylene polymers in the mixture can vary. The weight ratio of the first polyisobutylene polymer to the second polyisobutylene polymer in the mixture can be 10:1 to 1:10, preferably 2:1 to 1:2, most preferably 3:2 to 2:3. In particularly preferred embodiments, the polyisobutylene polymer of the contact adhesive consists of 40 to 60% by weight Oppanol® B10 (for example Oppanol® B10 SFN) and 60 to 40% by weight Oppanol® B50SF.

Preferably, the adhesive layer improved according to the invention additionally contains polybutene. Suitable average molecular weights $M_N$ of polybutene are for example in the range of about 500 to 10,000 g/mol. Also polybutene preferably is present in a mixture of different average molecular weights. A preferred mixture is that of (1) polybutene with an average molecular weight $M_N$ of about 900 g/mol (e.g. Indopol® H-100, with an average molecular weight $M_N$=910 g/mol, available from Ineos) and (2) polybutene with an average molecular weight $M_N$ of about 6,000 g/mol (e.g. Indopol® H-18000, available from Ineos).

Another preferred mixture is that of (1) polybutene with an average molecular weight $M_N$ of about 900 g/mol (e.g. Indopol® H-100, with an average molecular weight $M_N$=910 g/mol, available from Ineos) and (2) polybutene with an average molecular weight $M_N$ of about 2,500 g/mol (e.g. Indopol® H-1900, available from Ineos).

Particularly preferred is the mixture of (1) polybutene with an average molecular weight $M_N$ of about 2,500 (e.g. Indopol® H-1900, available from Ineos) and (2) polybutene with an average molecular weight $M_N$ of about 6,000 g/mol (e.g. Indopol® H-18000). It is within the knowledge of the skilled person to mix the various molecular weights in a suitable ratio such that the desired properties of the adhesive layer in terms of adhesiveness and release rate of the active substance are achieved in the system.

The proportions of two polybutenes in the adhesive layer can vary. The weight ratio of the first polybutene to the second polybutene is preferably 2:1 to 1:2, most preferably 3:2 to 2:3. In a particularly preferred embodiment the polybutene polymer in the adhesive layer consists of 40% by weight of polybutene with an average molecular weight $M_N$ of about 2,500 g/mol and about 60% by weight of polybutene with an average molecular weight $M_N$ of 6,000 g/mol.

The "average molecular weight $M_N$" is the number-average molar mass and can be determined according to "American Standard" ASTM D3536-91 or ASTM D5296-05.

The constituents of the improved adhesive layer according to the invention, polyisobutylene and polybutene, are preferably present in a weight ratio of 4:1 to 1:2, more preferably 3:1 to 1:2. For example, polyisobutylene and polybutene can be present in a weight ration of about 1:1. In another embodiment, polyisobutylene and polybutene are present in a weight ratio of about 7:3.

Preferably, the adhesive layer contains about 10 to about 90% by weight, preferably about 25 to about 75% by weight, most preferably about 40 to about 70% by weight of polyisobutylene (e.g., about 50% by weight or about 70% by weight), based on the total weight of the adhesive layer. These proportions indicate the total content of polyisobutylene or polyisobutylene mixture in the adhesive layer. Preferably, the adhesive layer also contains about 5 to about 80% by weight, preferably about 15 to about 60% by weight, most preferably about 25 to about 50% by weight polybutene (e.g. about 50% by weight or about 30% by weight), based on the total weight of the adhesive layer. These proportions indicate the total content of polybutene or polybutene mixture, respectively, in the adhesive layer.

In a preferred embodiment, the adhesive layer does not contain any acrylate polymer and acrylate copolymer.

The thickness of the adhesive layer (dry thickness) is not particularly limited. It can be in a range of about 10-300 µm, or in a range of 70-140 µm. The absolute amount of the adhesive layer can be about 10-50 g/m², or 20-40 g/m², without being limited thereto.

Generally, the adhesive layer contains 60-100% by weight of the contact adhesive (e.g. polyisobutylene) or the mixture of contact adhesives, respectively, including adhesive enhancer (e.g. polybutene). Further possible constituents of the adhesive layer are plasticizers and gel-forming agents.

Suitable plasticizers are known in the prior art, with these preferably being mineral oil, neutral oil, paraffin, linseed oil, octyl palmitate, squalene, squalane, silicone oil, isobutyl myristate, isostearyl alcohol, and/or oleyl alcohol, more preferably mineral oil, neutral oil, and/or paraffin. Mineral oils are colorless clear hydrocarbons. They are recovered from the distillation fractions of petroleum that boil above about 300° C. and are liberated from solid hydrocarbons by cooling. By suitable fractionation, mineral oils can be recovered that are liquid at body temperature, that is at about 35-37° C. and are solid at low temperatures, in particular at temperatures below 20° C. The choice of the mineral oil with a liquefaction point of about 30-35° C. is preferred. Particularly preferred are the paraffins and mineral oils that correspond to the requirements of the Ph. Eur. 6 and/or USP 32-NF 27.

In general, the plasticizer is present in the adhesive layer in an amount in the range of 0-40% by weight, or 1-10% by weight, or in the range of 2-5% by weight, for example 2% by weight, based on the total weight of the adhesive layer.

Preferably, the gel-forming agent is a gel-forming agent with a particulate structure and a high concentration of polar groups on its surface. These cause correspondingly high interfacial tensions towards the oils that are partially compensated by agglomeration of the particles among themselves into gel skeletons. Accordingly, the gel skeletons are always the more solid the bigger the difference in polarity is between the oils and the surface of the skeleton forming agent. According to the invention it is preferred to use highly disperse silica or pyrogenic silicic acid as the gel-forming agent. The size of the particles preferably is in the nanometer range and is for example in the range of 400-1500 nm, in particular in the range of 500-1000 nm. Pyrogenic silicic acid is for example sold under the designation CAB-O-SIL® and is a known thickener for mineral oils. Another example of suitable gel-forming agents is bentonite. Also, the sodium carbomer known as a gel-forming agent can be used.

The gel-forming agent is preferably used in an amount of 0-4.0% by weight, more preferably 0.1-2.0% by weight, still more preferably 0.5-2.0% by weight, based on the weight of the adhesive layer.

In a particularly preferred embodiment of the TTS according to the invention the adhesive layer consists of 99.5% by weight of mixtures of polyisobutylene with different molecular weights and polybutene with different molecular weights and of 0.5% by weight of a gel-forming agent, preferably highly disperse silica or pyrogenic silicic acid, based on the total weight of the adhesive layer.

Cover Layer

Preferably, the cover layer of the TTS according to the invention is occlusive, that is ending. In a preferred embodiment such cover layers can consist of polyolefins, in particular polyethylene, or polyesters as well as polyurethanes. Also layers containing several different polymers arranged on top of each other can preferably be used. Suitable materials comprise polyolefin, cellophan, cellulose acetate, ethyl cellulose, vinyl acetate-vinyl chloride copolymers provided with plasticizers, ethylene-vinylacetate copolymers, polyethylene terephthalate, nylon, polyethylene, polypropylene, polyvinylidene chloride, ethylene-methacrylate copolymers, paper which can optionally be coated, textile tissue, aluminum foil, and polymer-metal composite materials. Polyester foils, such as polyethylene terephthalate foils are particularly preferred. As is common in the prior art, the thickness of the back layer may be for example 10 μm to 100 μm, for example about 40 μm (nominal thickness). Especially preferred are composite foils of pigmented PE, PETP, and aluminum.

Pull-off Layer

According to the invention, on the adhesive layer there is a pull-off layer, also referred to as "release liner". Preferably, said pull-off layer is prepared from polymeric material that optionally can also be metallized. Examples of preferably used materials are polyurethanes, polyvinylacetate, polyvinylidene chloride, polypropylene, polycarbonate, polystyrene, polyethylene, polyethylene terephthalate, polybutylene terephthalate as well as papar that is optionally surface coated with corresponding polymers. Preferably it is a pull-off layer that is fluoropolymer-coated or siliconized on one or both sides. Particularly preferred are usual fluoropolymer-coated or siliconized polyester foils, such as the one-sided siliconized commercial products Primeliner 100 μm and Perlasic LF 75 μm (Loparex, NL and Perlen Converting AG, Switzerland) or the one-sided fluoropolymer-coated products such as e.g. ScotchPak 1022 (3M Drug delivery).

FURTHER ASPECTS AND EMBODIMENTS

A particularly preferred embodiment of the TTS according to the invention is a TTS for administering an active substance through the skin comprising:

a) a cover layer,
b) an active substance layer on the cover layer that contains 30-50% by weight of the active substance and 50-70% by weight of the polymer matrix, based on the total weight of the active substance layer, wherein the polymer matrix substantially consists of an acrylate polymer without hydroxyl groups and without carboxyl groups, or substantially consists of an acrylate copolymer without hydroxyl groups and without carboxyl groups, and wherein the active substance is rivastigmine or a physiologically compatible salt, hydrate, solvate, or derivative thereof;
c) a membrane on the active substance layer that controls the release of the rivastigmine;
d) an adhesive layer on the membrane that consists of 0-1% by weight silica and 99-100% by weight of a mixture of a polyisobutylene polymer with an average molecular weight $M_V$ of about 40,000 g/mol, a polyisobutylene polymer with an average molecular weight $M_V$ of about 400,000 g/mol, a polybutene polymer with an average molecular weight $M_N$ of about 2,500 g/mol and a polybutene polymer with an average molecular weight $M_N$ of about 6,000 g/mol; and
e) a pull-off layer on the adhesive layer.

Particularly, the amount of antioxidant in the entire formulation of this embodiment without cover and pull-off layer is less than 0.1% by weight, preferably less than 0.01%.

In a particularly preferred embodiment the TTS according to the invention has no antioxidant selected from the group consisting of vitamin E and esters thereof, butylated hydroxytoluene and butylated hydroxyanisole.

Preferably, the TTS according to the invention has a substantially linear permeation profile. Here, the permeation is substantially linear over a period of at least 24 hours, preferably at least 48 hours, more preferably at least 72 hours, most preferably at least 96 hours, or at least 120 hours, or at least 144 hours, or at least 168 hours. The permeation can be determined by permeation tests per se known to the skilled person, for example by the in vitro permeation test according to "OECD GUIDELINE FOR THE TESTING OF CHEMICALS. Skin Absorption: in vitro method." Test Guideline 428. Adopted 13 Apr. 2004: 1-8. Preferably, the term "substantially linear" means that the permeation rate, expressed in amount permeated per unit of time and unit area, is not significantly changed over a prolonged time interval so that the permeation profile has a substantially linear course. However, in particular in the initial phase a so-called period of latency can occur, wherein the permeation not yet has the constant permeation rate, and moreover, the permeation rate may be reduced at very late time points due to a very strong discharge of the system.

In a particular embodiment the average release rate in vivo is between 0.1 mg/d/cm$^2$ and 2 mg/d/cm$^2$, preferably between 0.2 mg/d/cm$^2$ and 1 mg/d/cm$^2$ and most preferably at least 0.3 mg/d/cm$^2$.

A further aspect of the present invention is to provide a method for the production of the TTS according to the invention. The method comprises i) the preparation of a component containing the active substance layer that contains the cover layer and the active substance layer, which is on the side of the cover layer that is supposed to be the side facing the skin;
ii) the preparation of a component containing the adhesive layer that contains the pull-off layer and the adhesive layer on the pull-off layer and optionally a membrane controlling the release of the active substance;
iii) laminating onto each other the components of i) and ii) such that the cover and pull-off layer in the cross-section of the finished TTS represent the opposing outermost layers.

One embodiment of the method comprises:

i) applying and optionally subsequent drying of a film of a composition forming the active substance layer, optionally in the form of a solution or dispersion in a suitable medium, onto the side of the cover layer supposed to be the side facing the skin, and optionally backing with the membrane controlling the release of the active substance:
ii) applying and optionally subsequent drying of a film of a composition forming the adhesive layer, optionally in the form of a solution or dispersion in a suitable medium, onto the pull-off layer; and iii) laminating onto each other the components of i) and ii) such that the cover and pull-off layer in the cross-section of the finished TTS represent the opposing outermost layers.

Another embodiment of the method comprises:

i) applying and optionally subsequent drying of a film of a composition forming the adhesive layer, optionally in the form of a solution or dispersion in a suitable medium, onto a siliconized pull-off foil ("intermediate liner") and backing with the cover layer, ii) puling off the siliconized pull-off foil ("intermediate liner") and backing with the membrane controlling the release of the active substance;

iii) applying and optionally subsequent drying a film of a composition forming the adhesive layer, optionally in the form of a solution or dispersion in a suitable medium, onto the pull-off layer; and iv) laminating onto each other the components of ii) and iii) such that the cover and pull-off layer in the cross-section of the finished TTS represent the opposing outermost layers.

The preparation of a preferred TTS may be performed by firstly dispersing or dissolving, respectively (unless the polymer is already dissolved) the components for the active substance layer, that is the active substance (preferably rivastigmine) and the matrix-forming polymer or copolymer, respectively, or a mixture thereof, in an organic solvent such as heptane or ethyl acetate. Typically, the matrix-forming polymer or copolymer or the mixture thereof is already present in a solvent. Here, according to the invention a polymer and/or copolymer is used that is as defined above in connection with the TTS according to the invention, that is a polymer and/or copolymer without hydroxyl groups and without carboxyl groups. The embodiments of the polymer matrix mentioned above as being preferred correspondingly apply to the method according to the invention. In the preparation of the active substance layer there is preferably used a volatile organic solvent. Then, said mixture is applied to the cover layer as a uniform layer and dried. In case that a membrane controlling the release of the active substance is to be applied, after the active substance layer is dried this can be applied to the side of the active substance layer opposite to the cover layer, instead of the "intermediate liner". Preferably, the component for the active substance layer for protection is provided with a foil, preferably a siliconized polyester foil, also referred to as "intermediate liner", that is applied to the side of the active substance layer opposite to the cover layer. Alternatively or equivalent, at first the mixture can also be applied to the "intermediate liner" and dried, with the cover layer being subsequently applied to the side of the active substance layer opposite to the "intermediate liner". The "intermediate liner" is removed right before the active substance layer component is fit together with the component containing the adhesive layer. Optionally, after pulling off the "intermediate liner" also the control membrane can be backed before the fitting with the adhesive layer is performed.

In a separate step, the adhesive layer is prepared by dispersing the polymer mixture forming the contact adhesive (and dissolved in an organic solvent), preferably polyisobutylene of different average molecular weights, optionally together with adhesive enhancer, gel-forming agent and/or the plasticizer in an organic solvent such as heptane. However, it is preferred that the contact adhesive and the adhesive enhancer and/or plasticizer are dissolved in the organic solvent and subsequently the gel-forming agent is dispersed in this solution. Then, said mixture is applied to the pull-off film and allowed to dry. The embodiments of the adhesive layer mentioned above as being preferred correspondingly apply to the method according to the invention.

The components obtained in these two process steps are subsequently laminated together, namely preferably such that the adhesive layer is directly applied to the active substance layer. In the embodiments where a membrane is used the adhesive layer is applied to the membrane. Subsequently, pieces of the desired size can be punched from the finished laminated foil and packaged.

In the individual process steps the organic solvents required to dissolve or disperse the respective components are removed by subjecting the products to increasing temperatures, optionally also using a partial vacuum.

A further aspect of the present invention is the use of a polymer or copolymer having neither amino groups nor hydroxyl groups nor carboxyl groups in a TTS containing rivastigmine that is suitable for an application period of at least two or at least three days (e.g. two, three, four, five, six, or seven days). The use of polyacrylates, acrylate-vinyl acetate copolymers, polyisobutylene, and styrene-butadiene copolymers as defined above is preferred. According to the invention, these polymers or copolymers represent the polymer matrix of the active substance layer in which the active substance rivastigmine is embedded.

A further aspect of the invention is the use of a polymer or copolymer having no free hydroxyl groups and no free carboxyl groups to stabilize rivastigmine in a TTS, or to reduce the degradation of rivastigmine in a TTS A further aspect of the invention is the use of a polymer or copolymer having neither free amino groups nor free hydroxyl groups nor free carboxyl groups to stabilize rivastigmine in a TTS, or to reduce the degradation of rivastigmine in a TTS.

Preferably, in the use according to the invention amino group-free, hydroxyl group-free, and carboxyl group-free polyacrylates and polyacrylate copolymers, such as acrylate-vinyl acetate copolymers are employed.

In a particularly preferred embodiment of the use according to the invention the acrylate-vinyl acetate copolymer Duro-Tak® 87-4098 is used.

In a further particularly preferred embodiment of the use according to the invention the acrylate polymer Duro-Tak® 87-9088 is used.

A further aspect of the present invention is the use of polyisobutylene and polybutene as exclusive constituents of the contact adhesive/adhesive enhancer in the adhesive layer of a TTS that is suitable for an application period of at least two or at least three days. Here, according to the preceding aspects of the present invention the polyisobutylene and polybutene preferably are present as mixtures of different average molecular weights.

A further aspect of the present invention is to provide the TTS according to the invention for the treatment of the Alzheimer's disease and Parkinson's dementia. Here, the TTS according to the invention is preferably prepared for an application period of at least two or at least three days. Longer application periods are also possible.

In the following, preferred embodiments of the TTS according to the invention are described with respect to experimental examples and their properties are determined in terms of the stability.

EXPLANATIONS OF THE FIGS. 1-7

In the following, parameter "n" indicates the number of repeats of the measurements performed leading to averaged results.

FIG. 1: Schematic cross-section of a rivastigmine TTS with membrane (not true to scale).

Figure 2:
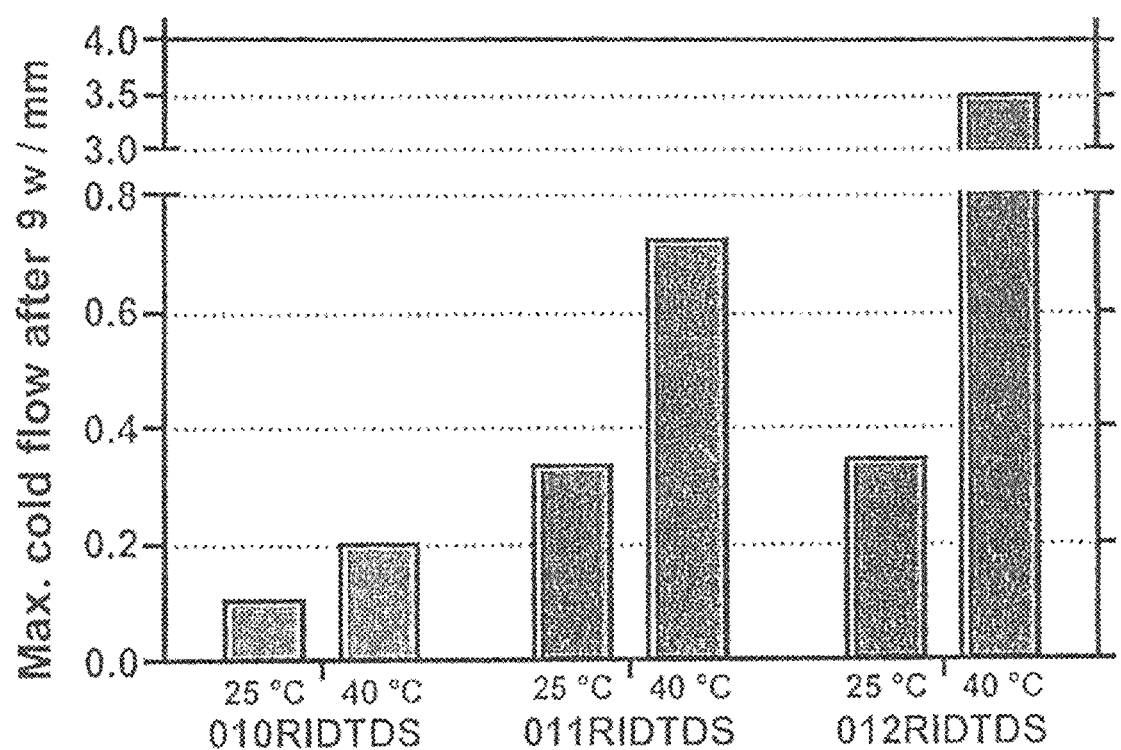

FIG. 2: Graph regarding the maximum cold flow of the active substance layers after 9 weeks of storage at 25° C./60% r.h. and 40° C./75% r.h. (n=2).

Figure 3:
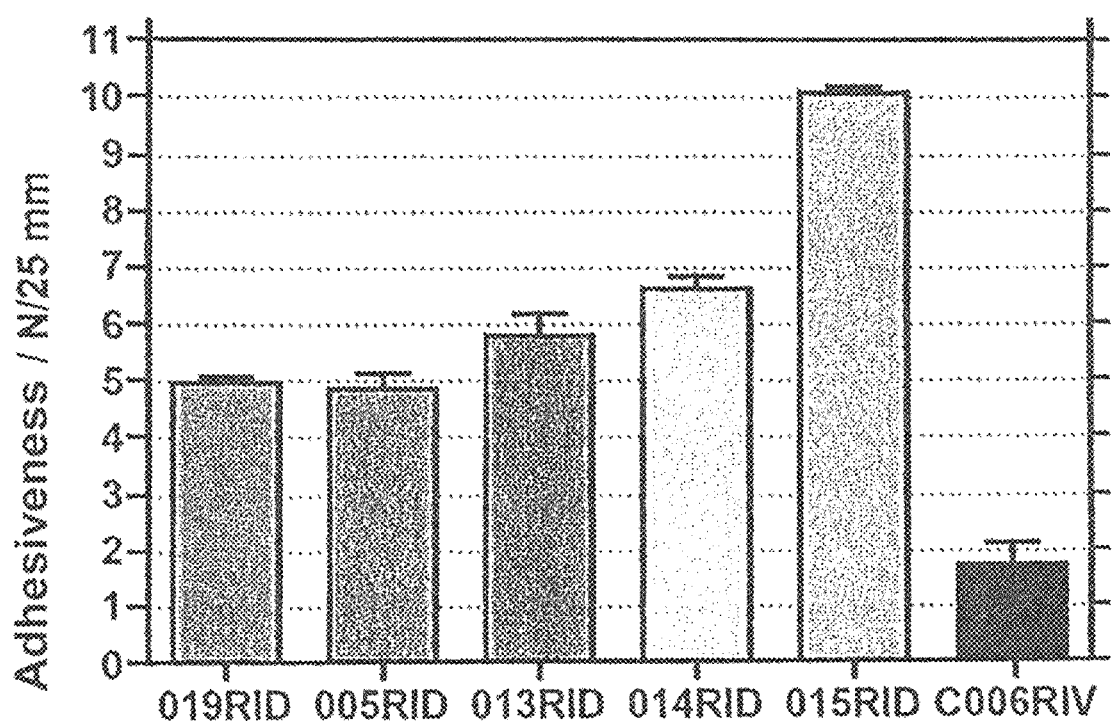

FIG. 3: Graph regarding the adhesiveness of the adhesive layers prepared according to the examples (n=3).

Figure 4:
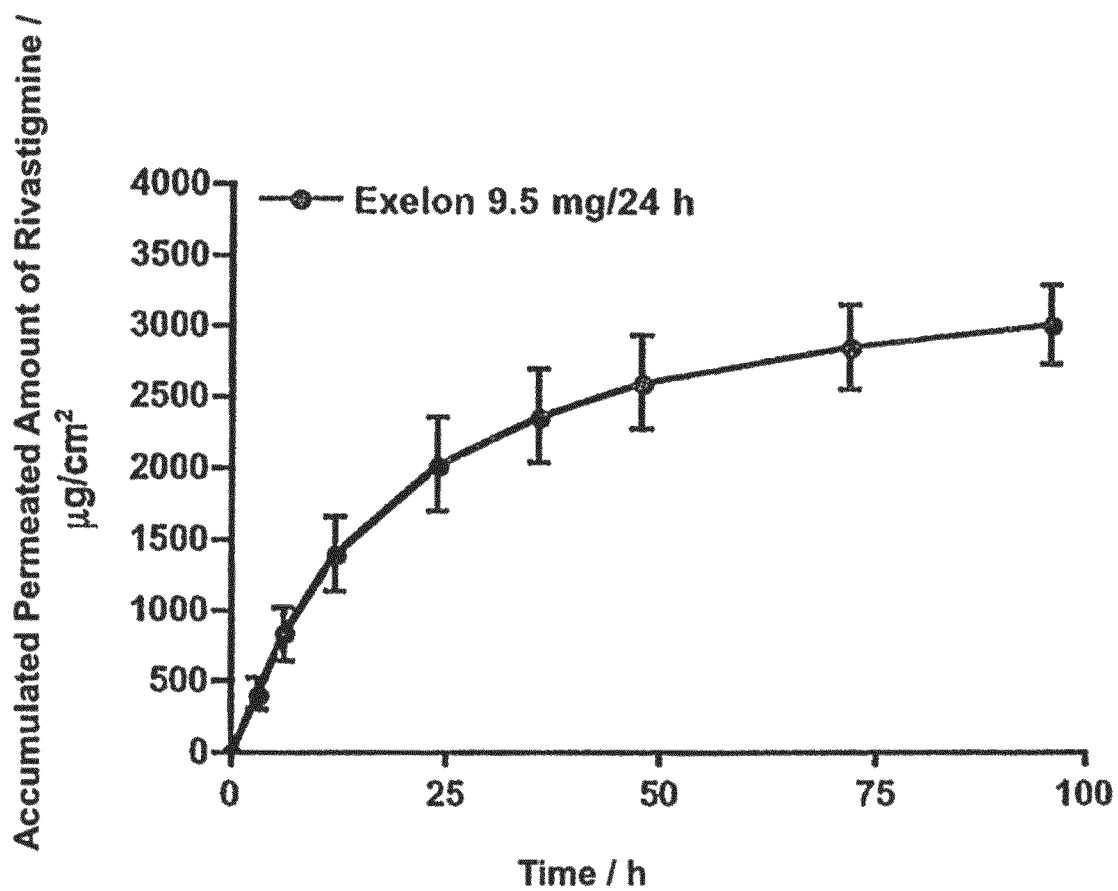

FIG. 4: in vitro permeation profile of rivastigmine from Exelon® (n=6).

Figure 5:
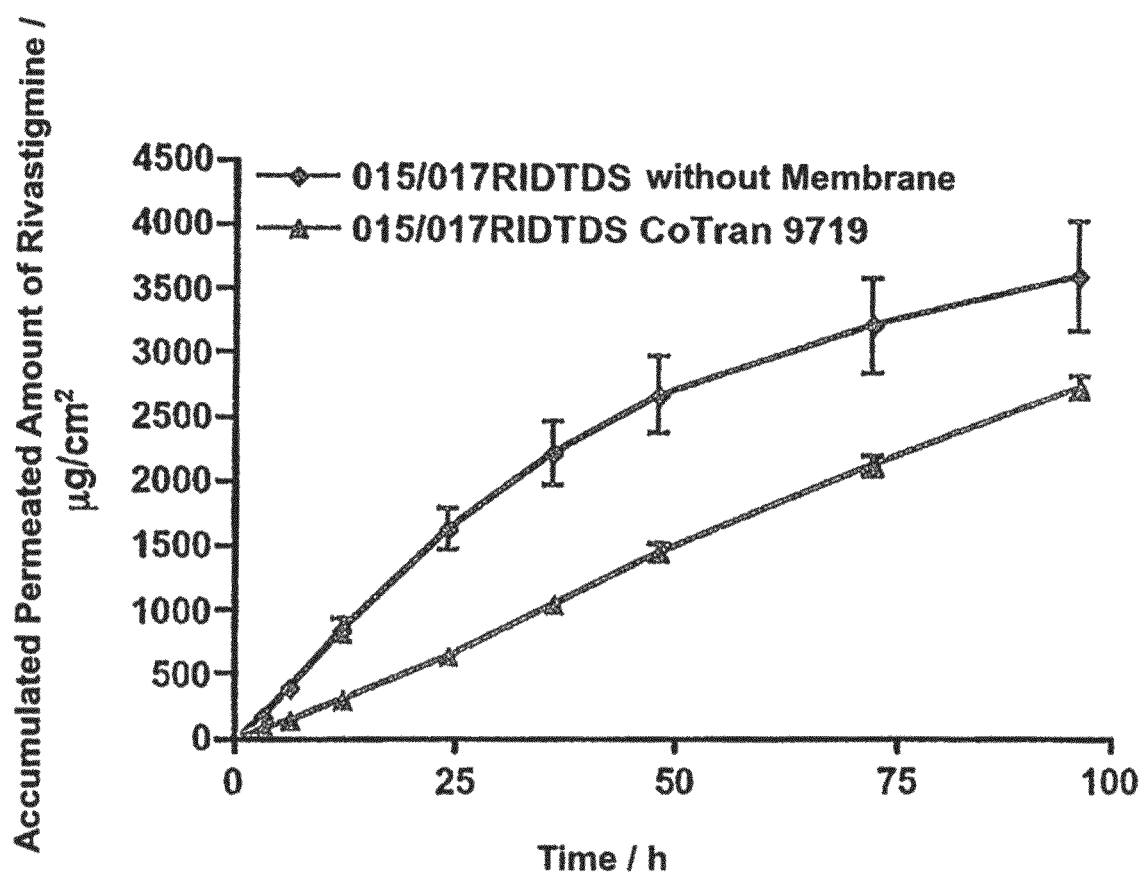

FIG. 5: In vitro permeation profiles of rivastigmine from two-layer laminates with and without membrane (n=4).

Figure 6:
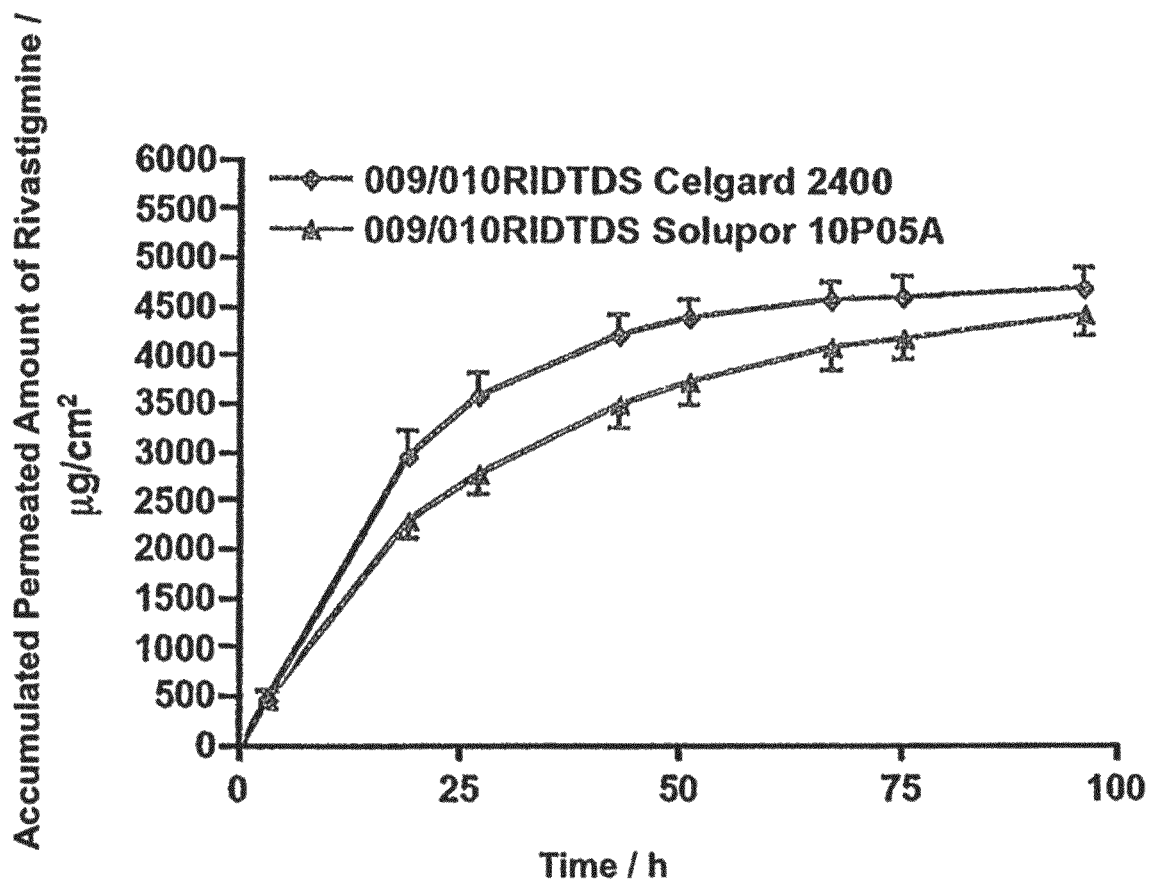

FIG. 6: In vitro permeation profiles of rivastigmine from two-layer laminates with adhesive layers based on a polyacrylate adhesive (n=4).

Figure 7:
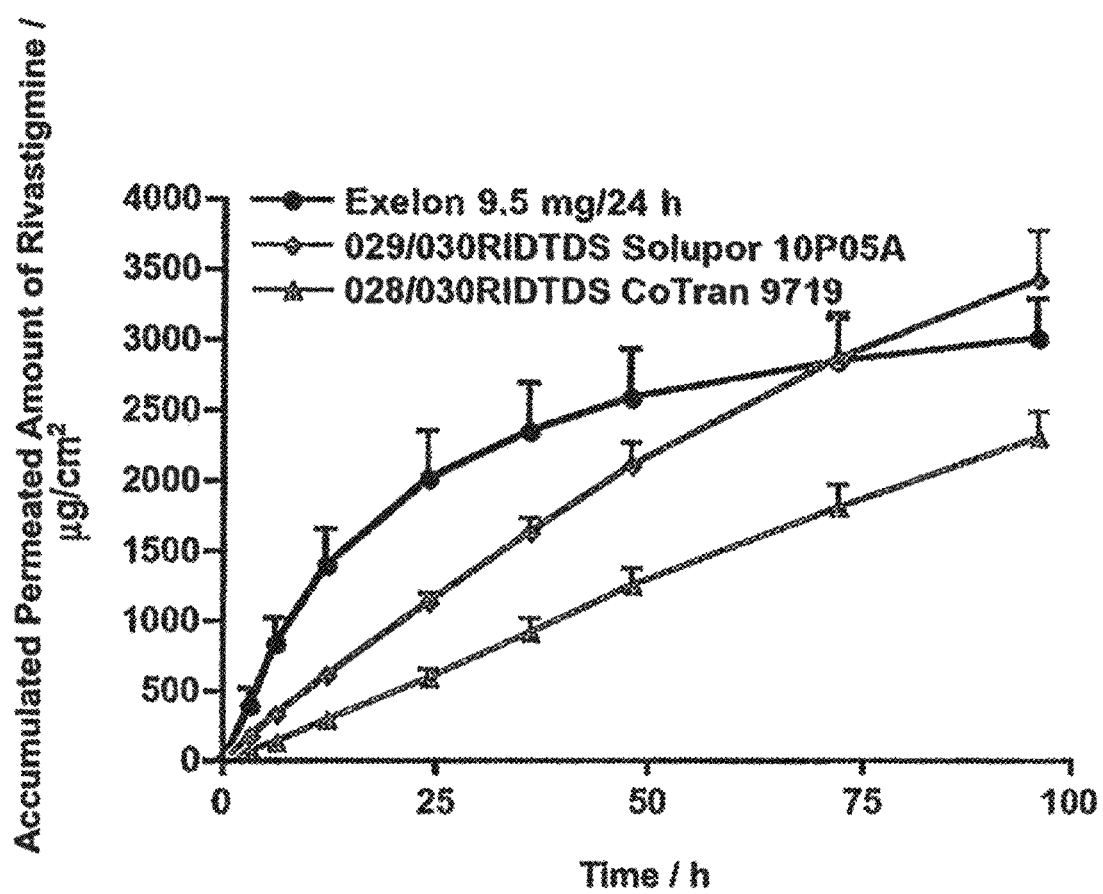

FIG. 7: In vitro permeation profiles of rivastigmine from two-layer laminates with different membranes and adhesive layers in comparison to Exelon® (n≥4).

Figure 8:
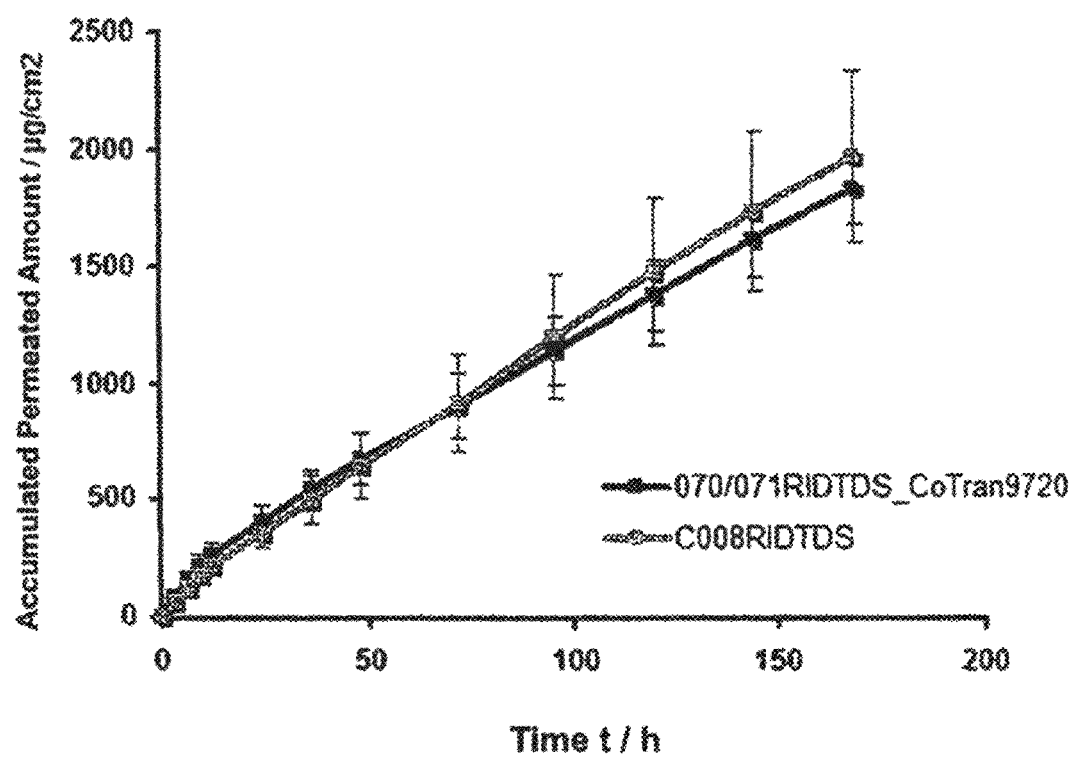

FIG. 8: In vitro permeation profiles of rivastigmine from two-layer laminates with different membranes (n≥4).

Figure 9:
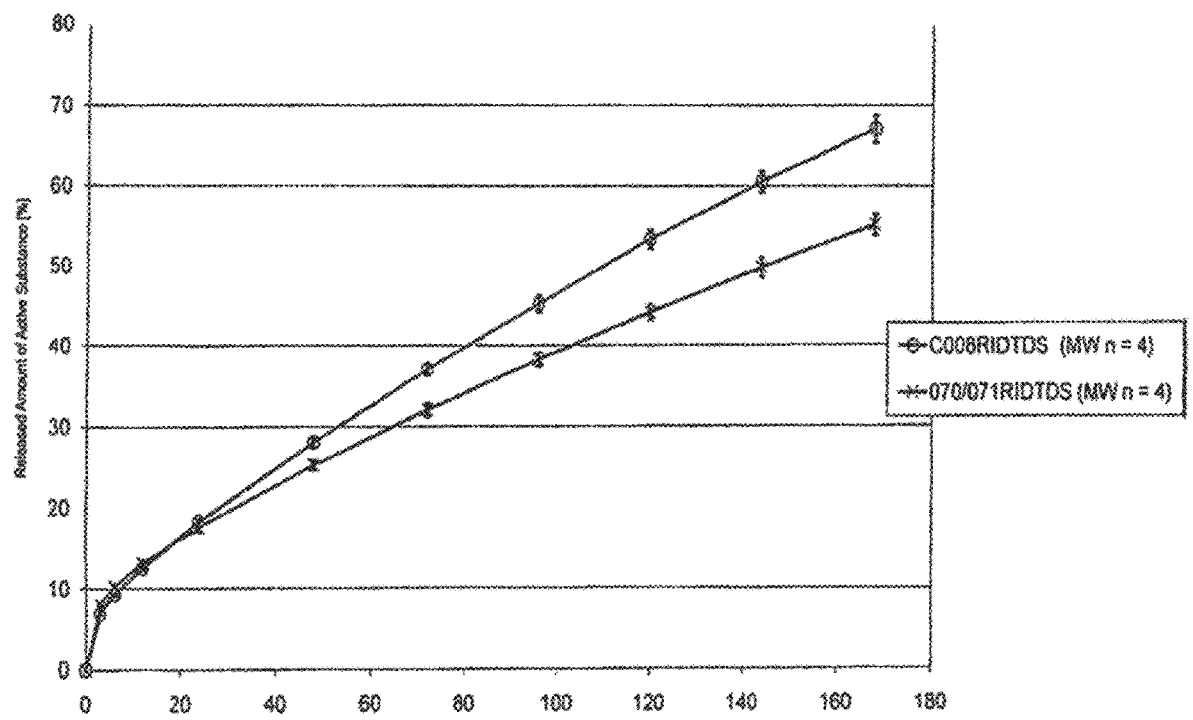

FIG. 9: In vitro release profile of rivastigmine from two-layer laminates with different membranes (n≥4).

EXAMPLES

The components used in the following formulation examples can be described in more detail as follows:

TABLE 1

Summary of the components of the formulation examples

| Component Designation | Chemical Description | Function |
| --- | --- | --- |
| Duro-Tak ® 87-4098 | Acrylate/Vinyl Acetate Copolymer | Matrix Polymer |
| Duro-Tak ® 87-9088 | Acrylate Copolymer | Matrix Polymer |
| Cab-O-Sil ® | Pyrogenic Silica | Get-forming Agent |
| Oppanol ® B10 | Polyisobutylene ($M_v$ = ca. 4 × $10^4$ g/mol) | Contact Adhesive |
| Oppanol ® B50 SF | Polyisobutylene ($M_v$ = ca. 4 × $10^5$ g/mol) | Contact Adhesive |
| Indopol H-100, H-1900, H-6.000, H-18.000 | Polybutene ($M_N$ = 910, 2,500, 4,200 or 6,000 g/mol) | Tackifier |
| Eudragit ® E100 | Acrylate Copolymer | Matrix Polymer |

Example 1

Preparation of Different Active Substance Layer Formulations

Three different active substance layer formulations containing rivastigmine base have been prepared. A summary of the constituents of the different formulations is given in table 2.

TABLE 2

Active Substance Layers used

| Charge | Active Substance Layer (R) | Matrix Weight mg/10 $cm^2$ |
| --- | --- | --- |
| 010RIDTDS | 40% Rivastigmine; 60% DT ® 87-9088 | 64 |
| 011RIDTDS | 40% Rivastigmine; 60% DT ® 87-4098 | 62 |
| 012RIDTDS | 40% Rivastigmine; 60% Eudragit ® E100 | 54 |

In FIG. 2, the results on the physical stability (cold flow) of the preceding reservoir formulations are given. The formulation with DT® 87-9088 (010RIDTDS) after 9 weeks of storage shows the lowest cold flow and thus, is particularly suitable as a matrix-forming agent for the active substance layer.

Example 2

Six different formulations of the adhesive layer have been prepared. A summary of the constituents of the different formulations is given in table 3.

TABLE 3

Adhesive Layers used

| Charge | Adhesive Layer (A) | Matrix Layer mg/10 $cm^2$ |
| --- | --- | --- |
| 019RIDTDS | 17.91% Oppanol ® B10 SFN; 31.84% Oppanol ® B50SF; 29.85% Indopol ® H-100; 19.90% Indopol ® H-1900; 0.50% Cab-O-Sil ® M5P | 30 |

TABLE 3-continued

Adhesive Layers used

| Charge | Adhesive Layer (A) | Matrix Layer mg/10 cm$^2$ |
|---|---|---|
| 005RIDTDS | 24.88% Oppanol ® B10 SFN; 24.88% Oppanol ® B50SF; 24.88% Indopol ® H-100; 24.88% Indopol ® H-1900; 0.50% Cab-O-Sil ® M5P | 32 |
| 013RIDTDS | 24.88% Oppanol ® B10 SFN; 24.88% Oppanol ® B50SF; 24.88% Indopol ® H-100; 24.88% Indopol ® H-6000; 0.50% Cab-O-Sil ® M5P | 32 |
| 014RIDTDS | 24.88% Oppanol ® B10 SFN; 24.88% Oppanol ® B50SF; 24.88% Indopol ® H-100; 24.88% Indopol ®H-18000; 0.50% Cab-O-Sil ® M5P | 30 |
| 015RIDTDS | 29.85% Oppanol ® B10 SFN; 19.90% Oppanol ® B50SF; 19.90% Indopol ® H-1900; 29.85% Indopol ® H-18000; 0.50% Cab-O-Sil ® M5P | 35 |
| C006RIVTDS | 64.5% Oppanol ® B10 SFN/B50SF (4/6); 35.0% Paraffin: 0.5% Cabo-O-Sil ® | 30 |

In FIG. 3, the results of measurements of the adhesiveness of the prepared adhesive layers are shown. These show that by the addition of Indopol® to the Oppanol® adhesive the adhesiveness is significantly improved in comparison to the use of paraffin. Moreover, the adhesiveness can be further increased and controlled by the specific selection of the molecular weights of the polymers used.

Example 3

Finally, six different charges of TTS formulations have been prepared. A summary of the composition of the different charges is made in table 4.

TABLE 4

Charges used:

| Charge | Active Substance Layer (R) | Adhesive Layer (A) | Membrane | Matrix Weight mg/10 cm$^2$ |
|---|---|---|---|---|
| 015/017 RIDTDS without Membrane | 40% Rivastigmine; 60% DT ® 87-9088 | 29.85% Oppanol ® B10 SFN 19.90% Oppanol ® B50SF 19.90% Indopol ® H-1900 29.85% Idopol ® H-18000 0.50% Cap-O-Sil M5P | — | 015RIDTDS (A): 35 017RIDTDS (R): 60 |
| 015/017 RIDTDS CoTran 9719 | 40% Rivastigmine; 60% DT ® 87-9088 | 29.85% Oppanol ® B10 SFN 19.90% Oppanol ® B50SF 19.90% Indopol ® H-1900 28.85% Indopol ® H-18000 0.50% Cap-O-Sil M5P | CoTran ™ 9719 | 015RIDTDS (A): 35 017RIDTDS (R): 60 |
| 009/010 RIDTDS Celgard 2400 | 40% Rivastigmine; 60% DT ® 87-9088 | 10% Rivastigmine; 90% DT ® 87-2516 | Celgard ® 2400 | 009RIDTDS (A): 33 010RIDTDS (R): 64 |
| 009/010 RIDTDS Solupor 10P05A | 40% Rivastigmine; 60% DT ® 87-9088 | 10% Rivastigmine; 90% DT ® 87-2516 | Solupor ® 10P05A | 009RIDTDS (A): 33 010RIDTDS (R): 64 |
| 029/030 RIDTDS Solupor 10P05A | 40% Rivastigmine; 60% DT ® 87-9088 | 20% Oppanol ® B10 SFN 30% Oppanol ® B50SF 30% Indopol ® H-100 20% Indopol ® H-1900 | Solupor ® 10P05A | 029RIDTDS (A): 34 030RIDTDS (R): 61 |
| 028/030 RIDTDS CoTran 9719 | 40% Rivastigmine; 60% DT ® 87-9088 | 30% Oppanol ® B10 SFN 20% Oppanol ® B50SF 20% Indopol ® | CoTran ™ 9719 | 028RIDTDS (A): 28 030RIDTDS (R): 61 |

TABLE 4-continued

Charges used:

| Charge | Active Substance Layer (R) | Adhesive Layer (A) | Membrane | Matrix Weight mg/10 cm² |
|---|---|---|---|---|
| 070/071 RIDTDS CoTran 9720 | 40% Rivastigmine; 60% DT ® 87-9088 | H-1900 30% Indopol ® H-18000 30% Oppanol ® B10 SFN 20% Oppanol ® B50SF 20% Indopol ® H-1900 30% Indopol ® H-18000 | CoTran ™ 9720 | 070RIDTDS (A): 30 071RIDTDS (R): 60 |

Preparation Method

1. Preparation of the Active Substance Layer

The acrylate adhesive has been added first and rivastigmine and ethyl acetate were weighted in. Subsequently, the components were mixed in sufficient ethyl acetate by means of a stirrer such that a spreadable homogeneous coating mass is formed.

The homogeneous coating mass was applied to a siliconized foil ("intermediate liner") as a thin film. The matrix film was dried at 60° C./20 min and 80° C./5 min and subsequently backed with a cover layer of PET.

Subsequently, the "intermediate liner" was pulled off and it was backed the control membrane.

2. Preparation of the Adhesive Layer and the Overall Laminate

The polyisobutylene adhesives were weighted in together and mixed. Subsequently, heptane and Cab-O-Sil® were added with stirring and stirred until the mass was homogeneous.

The mass was applied to a pull-off layer ("release liner") as a thin film and subsequently, the solvents were removed at 60° C./20 min and 80° C./5 min. After drying, the laminate is backed with an active substance layer.

Patches of suitable size were punched from the obtained laminate.

3. In vitro Mouse Skin Permeation Test

With the charges of table 4 and the commercial product Exelon® TDS, a one-day formulation, in vitro mouse skin permeation tests have been performed.

The results of these tests are given in FIGS. 4 to 7. FIG. 4 shows the permeation profile of rivastigmine from the commercially available Exelon® TDS. The curve trace in FIG. 4 clearly shows that the delivery rate of rivastigmine significantly decreases already after 24 hours. Thus, this system does not ensure the continuous and uniform active substance delivery over an application period of more than 24 hours.

FIG. 5 shows that a continuous and uniform active substance delivery for several days will only be permitted by the interposed membrane.

The formulation charges 009/010RIDTDS Celgard® 2400 and 009/010RIDTDS Solupor® 10P05A that contain polyacrylate as the matrix-forming agent for the adhesive layer surprisingly had a similar kinetics compared with that of Exelon® TDS (cf. FIGS. 4 and 6). This shows that polymers from the group of the polyacrylates and their copolymers are not suitable as matrix-forming agent for the adhesive layer, since they do not ensure a sufficient control of the active substance delivery over the application time of several days even with an interposed membrane.

FIGS. 5 and 7 show that by the combination of a membrane controlling the release of the active substance and an adhesive layer based on a polyisobutylene/polybutene mixture a control of the medicinal drug delivery over a time interval of several days is permitted.

FIG. 8 shows that with the two formulations "C008RIDTDS" and "070/071 RIDTDS CoTran 9720" a uniform linear permeation profile over seven days is achieved. Thus, these formulations are particularly suitable as 5-day patches. 6-day patches and 7-day patches. The formulation "C008RIDTDS" is derived from a clinical charge and has the same composition as formulation I (060/062RIDTDS_Cotran9719) described in example 4.

4. In vitro Release

The in vitro release was determined with the "Disk assembly Method" according to Ph. Eur. 5.0 <2.9.4>.

FIG. 9 shows that both formulations "C008RIDTDS" and "070/071 RIDTDS CoTran 9720" exhibit a uniform release of the active substance over at least seven days.

Example 4

Stability Test

According to the method mentioned above still two further formulations have been prepared:

TABLE 5

| | Formulation I (060/062RIDTDS_Cotran9719) | Formulation II (058/062RIDTDS_Cotran9728) |
|---|---|---|
| Active Substance Layer 60 g/m² | Rivastigmine (40%) DT ® 87-9088 (60%) | Rivastigmine (40%) DT ® 87-9088 (60%) |
| Membrane | CoTran ™ 9719 | CoTran ™ 9728 |
| Adhesive Layer 30 g/m² | Oppanol ® B10 SFN (30%) Oppanol ® B50 SF (20%) Indopol ® H-1900 (20%) Indopol ® H-18000 (30%) | Oppanol ® B10 SFN (30%) Oppanol ® B50 SF (40%) Indopol ® H-1900 (30%) |

The punched TTS were sealed in begs of aluminum composite foils and each stored for at least one month at 25° C. and 60% relative air humidity, or at 40° C. and 75% relative air humidity, respectively. Subsequently, the content of optionally impurities formed as a consequence of the decomposition of rivastigmine was determined by means of HPLC and UV absorption.

The TTS according to the invention showed an excellent stability over several months. After storage, only very low amounts of impurities/decomposition products were identified, although the active substance layer did not contain any antioxidants. This was achieved by the employment of a polymer matrix without hydroxyl groups and without carboxyl groups.

The results are summarized in the following table 6:

| | Charge | Temperature ° C./% r.h. | Initial | 1 Month | 2 Months | 3 Months |
|---|---|---|---|---|---|---|
| Purity n = 3 | 060/062RIDTDS_CoTran9719 | 25/60 | Imp. 1: 0.04% (<RL); Imp. 4: 0.02% (<RL); Imp. 5: 0.05% (<RL); | Imp. 1: 0.05% (<RL); Imp. 4: 0.08% (<RL); Imp. 5: 0.14%; | Imp. 1: 0.02% (<RL); Imp. 4: 0.07% (<RL); Imp. 5: 0.18%; | Imp. 1: 0.02% (<RL); RRT = 0.84: 0.01% (<RL); Imp. 2: 0.02% (<RL); |
| | | | → Sum: 0.0% | → Sum: 0.14% | → Sum: 0.18% | Imp. 4: 0.08% (<RL); Imp. 5: 0.17%; |
| | | | | | | → Sum: 0.17% |
| | | 40/75 | | Imp. 1: 0.04% (<RL); RRT = 0.85: 0.06% (<RL); Imp. 2: 0.02% (<RL); Imp. 4: 0.11%; Imp. 5: 0.23% (<RL); | | |
| | | | | → Sum: 0.34% | | |
| | 058/062RIDTDS_CoTran9728 | 25/60 | Imp. 1: 0.04% (<RL); Imp. 4: 0.02% (<RL); Imp. 5: 0.05% (<RL); | Imp. 1: 0.05% (<RL); Imp. 4: 0.05% (<RL); Imp. 5: 0.15%; | Imp. 1: 0.02% (<RL); Imp. 4: 0.06% (<RL); Imp. 5: 0.18%; | Imp. 1: 0.02% (<RL); RRT = 0.84: 0.02% (<RL); Imp. 2: 0.02% (<RL); |
| | | | → Sum: 0.0% | → Sum: 0.15% | → Sum: 0.18% | Imp. 4: 0.08% (<RL); Imp. 5: 0.18%; |
| | | | | | | → Sum: 0.18% |
| | | 40/75 | | Imp. 1: 0.05% (<RL); RRT = 0.85: 0.04% (<RL); Imp. 2: 0.03% (<RL); Imp. 4: 0.09% (<RL); Imp. 5: 0.22%; | | |
| | | | | → Sum: 0.22% | | |

RL = "Reporting Limit" (detection limit)
RRT = relative retention time (HPLC)

The invention claimed is:

1. A transdermal therapeutic system for administering an active substance through the skin comprising the layers arranged in the following order with respect to each other:
   a) a cover layer;
   b) an active substance layer comprising a polymer matrix containing a polymer or polymers and the active substance;
   c) a membrane controlling the release of the active substance, wherein the membrane is a non-porous membrane;
   d) an adhesive layer comprising a contact adhesive; and
   e) a pull-off layer;
wherein the active substance is rivastigmine or a physiologically compatible salt, hydrate, solvate, or derivative thereof, wherein the polymer matrix does not contain any free hydroxyl groups and free carboxyl groups.

2. The transdermal therapeutic system according to claim 1, characterized in that the active substance layer does not contain any free hydroxyl groups and free carboxyl groups.

3. The transdermal therapeutic system according to claim 1, characterized in that (i) it does not contain any tocopherols; and/or (ii) it does not contain any antioxidant selected from the group consisting of tocopherols, butylated hydroxyanisole, and butylated hydroxytoluene; and/or (iii) it does not contain any antioxidant.

4. The transdermal therapeutic system according to claim 1, characterized in that the contact adhesive contains a polyisobutylene or a mixture of several polyisobutylenes, and optionally a polybutene or a mixture of several polybutenes.

5. The transdermal therapeutic system according to claim 1, wherein the adhesive layer contains 98-100% by weight of the contact adhesive including polybutene, and 0-2.0% by weight of a gel-forming agent, based on the total weight of the adhesive layer.

6. The transdermal therapeutic system according to claim 1, characterized in that the contact adhesive consists of at least two polyisobutylenes with different average molecular weights and at least two polybutenes with different average molecular weights.

7. The transdermal therapeutic system according to claim 6, characterized in that the first polyisobutylene polymer has an average molecular weight $M_v$ of about 40,000 g/mol and the second polyisobutylene polymer has an average molecular weight $M_v$ of about 400,000 g/mol.

8. The transdermal therapeutic system according to claim 6, characterized in that the first polybutene polymer has an average molecular weight $M_n$ in the range of 700-2,800 g/mol and the second polybutene polymer has an average molecular weight $M_n$ in the range of 2,200-6,500 g/mol.

9. The transdermal therapeutic system according to claim 1, wherein the active substance layer contains 30-50% by weight of the active substance and 50-70% by weight of the polymer matrix, based on the total weight of the active substance layer.

10. The transdermal therapeutic system according to claim 1, wherein the polymer matrix of the active substance layer comprises at least one polymer and/or copolymer without free hydroxyl groups and without free carboxyl groups selected from the group consisting of polyacrylates, acrylate-vinyl acetate copolymers, polyisobutylene, styrene-butadiene copolymers, and mixtures thereof.

11. The transdermal therapeutic system according to claim 1, characterized in that the transdermal therapeutic system shows a substantially linear permeation profile of the active substance over a period of at least 48 hours.

12. The transdermal therapeutic system according to claim 1, characterized in that the membrane controlling the release of the active substance substantially consists of polyethylene.

13. The transdermal therapeutic system according to claim 1, characterized in that it shows a substantially linear skin permeation of the active substance over a period of at least 48 hours, as measured by an in vitro skin permeation test.

14. The transdermal therapeutic system according to claim 1, wherein the non-porous membrane controlling the release of the active substance substantially consists of a polyethylene and has a thickness of about 40 to 80 μm, or a polyethylene with about 19.0% vinyl acetate.

15. The transdermal therapeutic system according to claim 14, wherein the non-porous membrane substantially consists of a polyethylene and has a thickness of about 40 to 50 μm.

16. The transdermal therapeutic system according to claim 1, wherein the adhesive layer does not contain any acrylate polymer and acrylate copolymer.

17. A transdermal therapeutic system for administering an active substance through the skin, comprising the layers arranged in the following order with respect to each other:
   a) a cover layer,
   b) an active substance layer comprising a polymer matrix containing the active substance,
   c) an adhesive layer comprising (1) a polyisobutylene or a mixture of several polyisobutylenes and (2) a polybutene or a mixture of several polybutenes; and
   d) a pull-off layer;
      wherein the active substance is rivastigmine or a physiologically compatible salt, hydrate, solvate, or derivative thereof, wherein a membrane controlling the release of the active substance is a non-porous membrane and is arranged between the active substance layer and the adhesive layer, and wherein the polymer matrix does not contain any free hydroxyl groups and free carboxyl groups.

18. The transdermal therapeutic system according to claim 17, characterized in that the adhesive layer comprises at least two polyisobutylenes with different average molecular weights and at least two polybutenes with different average molecular weights.

19. The transdermal therapeutic system according to claim 18, characterized in that the first polyisobutylene polymer has an average molecular weight $M_v$ of about 40,000 g/mol and the second polyisobutylene polymer has an average molecular weight $M_v$ of about 400,000 g/mol.

20. The transdermal therapeutic system according to claim 18, characterized in that the first polybutene polymer has an average molecular weight $M_n$ in the range of 700-2,800 g/mol and the second polybutene polymer has an average molecular weight $M_n$ in the range of 2,200-6,500 g/mol.

21. The transdermal therapeutic system according to claim 17, wherein the active substance layer contains 30-50% by weight of the active substance and 50-70% by weight of the polymer matrix, based on the total weight of the active substance layer.

22. The transdermal therapeutic system according to claim 17, characterized in that the membrane controlling the release of the active substance substantially consists of polyethylene or polyethylene and vinyl acetate.

23. The transdermal therapeutic system according to claim 17, characterized in that it does not contain tocopherols; and/or (ii) it does not contain any antioxidant selected from the group consisting of tocopherols, butylated hydroxyanisole, and butylated hydroxytoluene; and/or (iii) it does not contain any antioxidant.

24. The transdermal therapeutic system of claim 17 for administering an active substance through the skin comprising:
   a) the cover layer,
   b) an the active substance layer on the cover layer that contains 30-50% by weight of the active substance and 50-70% by weight of the polymer matrix, based on the total weight of the active substance layer, wherein the polymer matrix substantially consists of an acrylate polymer without hydroxyl groups and without carboxyl groups, or substantially consists of an acrylate copolymer without hydroxyl groups and without carboxyl groups, and wherein the active substance is rivastigmine or a physiologically compatible salt, hydrate, solvate, or derivative thereof;
   c) a membrane on the active substance layer that controls the release of the rivastigmine;
   d) an the adhesive layer on the membrane that consists of 0-1% by weight silica and 99-100% by weight of a mixture of a polyisobutylene polymer with an average molecular weight $M_v$ of about 40,000 g/mol, a polyisobutylene polymer with an average molecular weight $M_v$ of about 400,000 g/mol, a polybutene polymer with an average molecular weight $M_N$ of about 2,500 g/mol and a polybutene polymer with an average molecular weight $M_N$ of about 6,000 g/mol; and
   e) a the pull-off layer on the adhesive layer.

25. A transdermal therapeutic system for administering an active substance through the skin comprising the layers arranged in the following order with respect to each other:
   a) a cover layer;
   b) an active substance layer comprising a polymer matrix containing the active substance;
   c) a membrane controlling the release of the active substance, wherein the membrane is a non-porous membrane;
   d) an adhesive layer comprising a contact adhesive; and
   e) a pull-off layer;
wherein the active substance is rivastigmine or a physiologically compatible salt, hydrate, solvate, or derivative thereof, characterized in that the transdermal therapeutic system does not contain tocopherols, and
wherein the polymer matrix does not contain any free hydroxyl groups and free carboxyl groups.

26. The transdermal therapeutic system according to claim 25, characterized in that it does not contain any antioxidant selected from the group consisting of tocopherols, butylated hydroxyanisole and butylated hydroxytoluene.

27. The transdermal therapeutic system according to claim 26, characterized in that it does not contain any antioxidant.

28. The transdermal therapeutic system according to claim 1, characterized in that it is suitable for the application over at least 2 days.

29. The transdermal therapeutic system of claim 25, having an average release rate of the active substance in vivo of between 0.1 mg/d/cm$^2$ and 2 mg/d/cm$^2$.

* * * * *